(12) United States Patent
Wellhöfer et al.

(10) Patent No.: US 9,301,876 B2
(45) Date of Patent: Apr. 5, 2016

(54) SYSTEM AND PROCESS FOR SURGICAL TREATMENT OF AN EYE AS WELL AS PROCESS FOR CALIBRATING A SYSTEM OF SUCH A TYPE

(75) Inventors: Armin Wellhöfer, Schwaig (DE); Christof Donitzky, Eckental (DE)

(73) Assignee: Wavelight GmbH (DE)

( * ) Notice: Subject to any disclaimer, the term of this patent is extended or adjusted under 35 U.S.C. 154(b) by 68 days.

(21) Appl. No.: 13/108,291

(22) Filed: May 16, 2011

(65) Prior Publication Data
US 2012/0296318 A1 Nov. 22, 2012

(51) Int. Cl.
*A61B 18/18* (2006.01)
*A61F 9/008* (2006.01)

(52) U.S. Cl.
CPC ... *A61F 9/00802* (2013.01); *A61F 2009/00855* (2013.01); *A61F 2009/00872* (2013.01)

(58) Field of Classification Search
CPC .......... A61F 9/008; A61F 2009/00872; A61F 9/00821
USPC ........................................... 606/4–6
See application file for complete search history.

(56) References Cited

U.S. PATENT DOCUMENTS

| | | | |
|---|---|---|---|
| 5,141,331 A | 8/1992 | Oehler et al. | |
| 6,116,737 A * | 9/2000 | Kern | 351/212 |
| RE37,504 E * | 1/2002 | Lin | 606/5 |
| 6,830,567 B2 * | 12/2004 | Schuele et al. | 606/4 |
| 6,918,904 B1 * | 7/2005 | Peyman | 606/5 |
| 8,160,846 B2 * | 4/2012 | Yilbas et al. | 703/2 |
| 2002/0026181 A1 * | 2/2002 | O'Donnell, Jr. | 606/10 |
| 2004/0236392 A1 | 11/2004 | Dick et al. | |
| 2006/0224146 A1 * | 10/2006 | Lin | 606/4 |
| 2007/0038202 A1 * | 2/2007 | Celestino et al. | 606/10 |
| 2007/0173792 A1 * | 7/2007 | Arnoldussen | 606/4 |
| 2008/0058781 A1 * | 3/2008 | Langeweyde et al. | 606/5 |
| 2009/0125005 A1 * | 5/2009 | Chernyak et al. | 606/5 |
| 2009/0240149 A1 * | 9/2009 | Peyman | 600/439 |
| 2011/0238046 A1 * | 9/2011 | Dick et al. | 606/5 |
| 2011/0276042 A1 * | 11/2011 | Dick et al. | 606/5 |
| 2012/0080586 A1 * | 4/2012 | Deisinger et al. | 250/252.1 |
| 2012/0089132 A1 * | 4/2012 | Dick et al. | 606/4 |
| 2012/0191005 A1 * | 7/2012 | Sobol et al. | 600/562 |

(Continued)

FOREIGN PATENT DOCUMENTS

JP  H10118108 A  12/1998
JP  2005-527317  9/2005

(Continued)

OTHER PUBLICATIONS

Brunsmann et al.; "Evaluation of thermal load during laser corneal refractive surgery using infrared thermography"; www.sciencedirect.com; Sep. 2010; pp. 342-347; vol. 53; Issue 5; Copyright 2010 Elsevier.

(Continued)

*Primary Examiner* — William Thomson
*Assistant Examiner* — John R Downey

(57) ABSTRACT

A system for surgical treatment of an eye includes a laser arrangement that is adapted to emit light with a wavelength and repetition-rate suitable for surgical treatment of the eye. The system further includes a temperature-registration device that is adapted to register the temperature of an object that is to be subjected to the light of the laser arrangement.

14 Claims, 2 Drawing Sheets

(56) References Cited

U.S. PATENT DOCUMENTS

2012/0209257 A1* 8/2012 van der Weide et al. ........ 606/23
2012/0323228 A1* 12/2012 Peyman .............................. 606/4

FOREIGN PATENT DOCUMENTS

| WO | 02/102262 A1 | 12/2002 |
| WO | 03017670 A1 | 2/2003 |
| WO | 2006/087180 A2 | 8/2006 |
| WO | 2010102246 | 9/2010 |

OTHER PUBLICATIONS

Fuisting et al.; "Transpupillary thermotherapy (TTT)—Review of the clinical indication spectrum"; www.sciencedirect.com; Medical Laser Application 25 (2010); pp. 214-222; Department of Ophthalmology, University Medical Center Hamburg-Eppendorf, Martinistr., Hamburg, Germany.

* cited by examiner

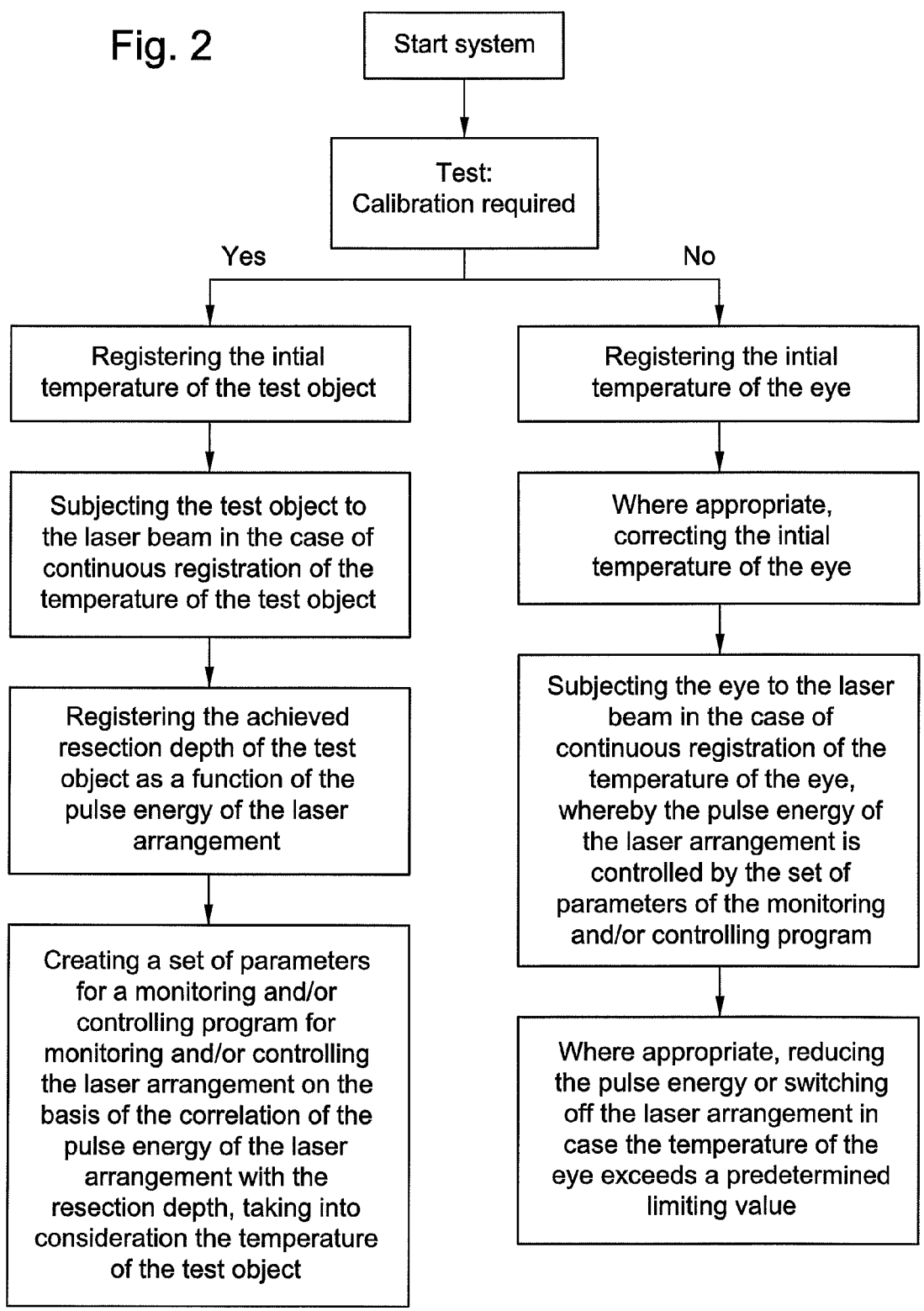

SYSTEM AND PROCESS FOR SURGICAL TREATMENT OF AN EYE AS WELL AS PROCESS FOR CALIBRATING A SYSTEM OF SUCH A TYPE The invention relates to a system and a process for surgical treatment of an eye, in particular using a laser with a high repetition-rate. The invention further relates to a process for calibrating a system of such a type for surgical treatment of an eye.

BACKGROUND OF THE INVENTION

In refractive eye surgery for the purpose of treating sight defects by photoablation of the cornea, argon-fluoride excimer lasers, which emit ultraviolet light with a wavelength of 193 nm, are customarily employed at present. Since the cornea exhibits a high absorption within this wavelength range, corneal tissue can be resected precisely with minimal stressing of adjacent tissue layers. The resection depth—that is to say, the thickness of the layer of corneal tissue resected by the laser—is controlled in this case by appropriate control of the pulse energy, in which connection the monitoring of the pulse energy has to be undertaken in such a way that harm to the patient by virtue of changes in the tissue adjacent to the corneal tissue to be resected is reliably avoided.

Excimer-laser systems that are used at the present time operate with repetition-rates from 200 Hz to 750 Hz. However, an increase in the laser frequency would enable a shortening of the duration of treatment, by virtue of which complications and the dehydration of the cornea during the operation could be minimised. Consequently efforts are being made in refractive eye surgery to bring excimer-laser systems into operation having an increased repetition-rate of up to 1050 Hz. However, the elevated frequency of the laser systems has to be taken into account in the control of the pulse energy, since otherwise damage to the eye being treated might not be reliably ruled out.

BRIEF SUMMARY OF THE INVENTION

An object underlying the invention is to specify a system and a process for surgical treatment of an eye that make it possible to avoid undesirable changes in tissue layers that are adjacent to tissue layers to be resected by means of a laser. Furthermore, an object underlying the invention is to make available a process for calibrating a system of such a type for surgical treatment of an eye.

This object is achieved by a system for surgical treatment of an eye, with the features of claim 1, a process for surgical treatment of an eye, with the features of claim 6, and a process for calibrating a system for surgical treatment of an eye, with the features of claim 11.

A system according to the invention for surgical treatment of an eye includes a laser arrangement that is adapted to emit light with a wavelength and repetition-rate suitable for surgical treatment of the eye. The laser arrangement may, for example, include an excimer laser, in particular an argon-fluoride excimer laser which emits ultraviolet light with a wavelength of 193 nm. In principle, in the case of the laser arrangement it may be a question of a conventional laser arrangement that operates with a repetition-rate from 200 Hz to 750 Hz. The laser arrangement is, however, preferentially capable of realising an elevated repetition-rate of, for example, 1050 Hz or more.

Furthermore, the treatment system includes a temperature-registration device that is adapted to register the temperature of an object that is to be subjected to the light of the laser arrangement. The temperature-registration device may be an arbitrary measuring device that is capable of registering the temperature of the object that is to be subjected to the light of the laser arrangement. The object may be the eye of a patient that is to be treated, but it may also be a test object that can be subjected to the light of the laser arrangement for the purpose of calibrating the system for surgical treatment of an eye, as will be elucidated in greater detail later. The temperature to be registered by means of the temperature-registration device may be the temperature of an object that is to be subjected to the light of the laser arrangement before the application of the light of the laser arrangement, or the temperature of an object that is to be subjected to the light of the laser arrangement during the application of the light of the laser arrangement.

The treatment system according to the invention makes it possible to take into consideration, in advantageous manner, the temperature of an object that is to be subjected to light from a laser arrangement in the course of the application of the light of the laser arrangement to the object. For example, with the aid of the system according to the invention the initial temperature of an eye to be treated or of a test object, i.e. the temperature that the eye or the test object exhibits before the treatment with the light emitted from the laser arrangement, can be taken into consideration in the course of the treatment of the eye or of the test object with the light of the laser arrangement. Alternatively or additionally thereto, the treatment system according to the invention makes it possible to register the effect that the light of the laser arrangement has on the temperature of an object that is subjected to the light of the laser arrangement. In particular, by means of the temperature-registration device an increase in the temperature of the object caused by the application of the light of the laser arrangement can be registered.

As a result, damage, caused by excessive temperatures, to an eye being treated by means of the treatment system according to the invention can, for example, be minimised or avoided. The risk of complications that is present in the course of surgical treatment of an eye can consequently be reduced. The furnishing of a system for surgical treatment of an eye with a temperature-registration device is sensible, in particular, when the system includes a laser arrangement that is capable of emitting light with a high repetition-rate of, for example, 1050 Hz, since a high repetition-rate of the laser arrangement has the consequence of an increased elevation of temperature in an object that is subjected to the light of the laser arrangement. The temperature-registration device may, however, also be employed in advantageous manner in a treatment system equipped with a conventional laser arrangement having a repetition-rate of, for example, 200 Hz to 750 Hz for the purpose of optimising the treatment procedure while avoiding thermal damage to the eye being treated.

The temperature-registration device of the treatment system according to the invention may be adapted to register the temperature of the object that is to be subjected to the light of the laser arrangement before the application of the light of the laser arrangement to the object. In other words, the temperature-registration device may have been set up to measure an initial temperature of the object that is to be subjected to the light of the laser arrangement. Additionally or alternatively thereto, the temperature-registration device may, however, be adapted to register the temperature of the object that is to be subjected to the light of the laser arrangement during the application of the light of the laser arrangement to the object. In particular, the temperature-registration device may be adapted to realise a continuous registration of the temperature of the object that is to be subjected to the light of the laser arrangement during the application of the light of the laser arrangement to the object.

The temperature-registration device may include a sensor, preferentially operating in non-contacting manner, for registering the temperature of an object that is to be subjected to the light of the laser arrangement. Alternatively, a furnishing of the temperature-registration device with a device for registering UV retroreflection from the object that is to be subjected to the laser light of the laser arrangement is also conceivable, on the basis of which an estimation of the temperature of the object that is to be subjected to the light of the laser arrangement is possible. The temperature-registration device is, however, preferentially equipped with a thermal-imaging camera.

A thermal-imaging camera is advantageous, in particular, when the temperature-registration device is to be employed for the purpose of registering the temperature of the object that is to be subjected to the light of the laser arrangement during the application of the light of the laser arrangement to the object, since the thermal-imaging camera does not impair the application of the light of the laser arrangement to the object but enables a registration of temperature in real time without difficulty. The IR radiation emitted from the object that is to be subjected to the light of the laser arrangement can be conducted directly to the thermal-imaging camera. If desired or required, however, at least one deflecting device, for example a deflecting mirror or such like, can also be arranged in the beam path of the IR radiation emitted from the object that is to be subjected to the light of the laser arrangement.

The system according to the invention for surgical treatment of an eye preferentially further includes a control device that has been set up to receive a temperature signal that is output by the temperature-registration device and to control the laser arrangement as a function of this temperature signal. For example, the control device may be adapted to receive a temperature signal that is characteristic of an averaged temperature over a defined area of the object that is to be subjected to the light of the laser arrangement, which, for example, may have a size of 20 mm×20 mm. The control device may be adapted to control the laser arrangement as a function of an initial temperature of the object that is to be subjected to the light of the laser arrangement, measured before the application of the light of the laser arrangement to the object. For example, the control arrangement may be adapted to adjust the pulse energy of the laser arrangement to the measured initial temperature of the object that is to be subjected to the light of the laser arrangement. Alternatively or additionally thereto, the control device may, however, also be adapted to control the laser arrangement during the application of the light of the laser arrangement to the object as a function of the temperature signal that is output by the temperature-registration device.

In particular, the control device may be adapted to reduce the pulse energy of the laser arrangement or to head for an ablation region again at a later time if the temperature, registered by the temperature-registration device, of the object that is subjected to the light of the laser arrangement exceeds a predetermined limiting value. If desired or required, the control device may also be adapted to switch off the laser arrangement if the temperature, registered by the temperature-registration device, of the object that is subjected to the light of the laser arrangement exceeds a predetermined limiting value. By virtue of such a configuration of the treatment system according to the invention, damage to an eye to be treated, caused by a undesirable increase in temperature, can be reduced or totally avoided. As a result, patients can be protected, for example, against eye damage that is caused by the failure of one scanner or of both scanners that guide(s) the laser beam over the surface of the eye being treated.

In the course of a process for surgical treatment of an eye the eye is subjected to light that is emitted from a laser arrangement with a wavelength and repetition-rate suitable for surgical treatment of the eye. The light emitted from the laser arrangement may, for example, be ultraviolet light with a wavelength of 193 m. The repetition-rate of the laser arrangement may amount to 200 Hz to 750 Hz but may also be distinctly higher and may be, for example, around 1050 Hz or more. Furthermore, in the course of the process for surgical treatment of an eye the temperature of the eye that is to be subjected to the light of the laser arrangement is registered.

The temperature of the eye that is to be subjected to the light of the laser arrangement can be registered by means of the temperature-registration device before and/or while the eye is subjected to the light of the laser arrangement. If the registration of temperature is undertaken before the application of the light of the laser arrangement to the eye, i.e. if the initial temperature of the eye is determined, measures can be taken, if required, for adjusting the temperature of the eye that is to be subjected to the light of the laser arrangement to a specified temperature. For example, the eye, in particular the cornea of the eye, can be cooled, in order to reduce the temperature thereof before the application of the light of the laser arrangement.

The temperature of the eye that is to be subjected to the light of the laser arrangement is preferentially registered in non-contacting manner with the aid of a thermal-imaging camera.

In a preferred embodiment of the process for surgical treatment of an eye the laser arrangement is controlled as a function of a temperature signal that is output by the temperature-registration device. For example, the control of the laser arrangement can be adjusted to a measured initial temperature of the eye that is to be subjected to the light of the laser arrangement. Additionally or alternatively thereto, the laser arrangement can be controlled during the surgical treatment of the eye, i.e. while the eye is being subjected to the light of the laser arrangement, as a function of a temperature signal that is output by the temperature-registration device.

In particular, the pulse energy of the laser arrangement can be reduced or an ablation region can be headed for again at a later time if the registered temperature of the eye that is being subjected to the light of the laser arrangement exceeds a predetermined limiting value. As a result, damage to the eye being treated that is brought about by excessive temperatures can be minimised or entirely prevented. If required, the laser arrangement may also be switched off completely if the registered temperature of the eye that is being subjected to the light of the laser arrangement exceeds a predetermined limiting value.

In the case of a process for calibrating a system for surgical treatment of an eye a test object is subjected to light that is emitted from a laser arrangement with a wavelength and repetition-rate suitable for surgical treatment of the eye. The light emitted from the laser arrangement may, for example, be ultraviolet light with a wavelength of 193 nm. The repetition-rate of the laser arrangement may amount to from 200 Hz to 750 Hz, but it may also be distinctly higher and may be, for example, around 1050 Hz or more. Furthermore, the temperature of the test object that is to be subjected to the light of the laser arrangement is registered. The test object may consist, for example, of a plastic material, in particular polymethyl methacrylate (PMMA), which is distinguished by a high absorption of the light emitted from the laser arrangement.

The temperature of the test object that is to be subjected to the light of the laser arrangement can be registered before and/or during the application of the light of the laser arrangement to the test object. In other words, in the process for calibrating a system for surgical treatment of an eye the initial temperature of the test object and/or the temperature of the test object can be taken into consideration during the application of the light of the laser arrangement to the test object.

The temperature of the test object that is to be subjected to the light of the laser arrangement is preferentially registered in non-contacting manner by means of a thermal-imaging camera.

A specified resection depth of the test object can be adjusted as a function of an initial temperature of the test object that is to be subjected to the light of the laser arrangement.

A set of parameters for a monitoring and/or controlling program for monitoring and/or controlling the laser arrangement during the surgical treatment of an eye is preferentially created as a function of a temperature signal that is output by the temperature-registration device. For example, the set of parameters for the monitoring and/or controlling program can be created as a function of a temperature signal that is output by the temperature-registration device and that characterises the initial temperature of the test object. Additionally or alternatively thereto, in the course of the creation of the set of parameters for the monitoring and/or controlling program a temperature signal that is output by the temperature-registration device and that characterises the temperature of the test object during the application of the light of the laser arrangement can be taken into consideration.

In particular, in the monitoring and/or controlling program for monitoring and/or controlling the laser arrangement during the surgical treatment of an eye a pulse energy of the laser arrangement that is required for achieving a desired treatment outcome is determined as a function of the temperature signal that is output by the temperature-registration device. For example, the pulse energy of the laser arrangement that is required in order to achieve a desired resection depth, i.e. a desired thickness of the tissue layer resected by the light of the laser arrangement, may have been saved in the monitoring and/or controlling program. For this purpose, within the scope of the process for calibrating the treatment system a correlation of the power of the laser arrangement with the achieved resection depth can be determined as a function of the temperature, and subsequently a correction of these data can be carried out, taking into consideration the material properties of the test object and of the part of the eye to be treated, for example the cornea of the eye.

BRIEF DESCRIPTION OF THE DRAWINGS

A preferred exemplary embodiment of the invention will now be elucidated in more detail on the basis of the appended, schematic drawings, in which FIG. 2 shows a flow chart that illustrates the steps of a process for calibrating a system for surgical treatment of an eye, and also of a process for surgical treatment of an eye.

DETAILED DESCRIPTION OF PREFERRED EMBODIMENTS

Figure 1:
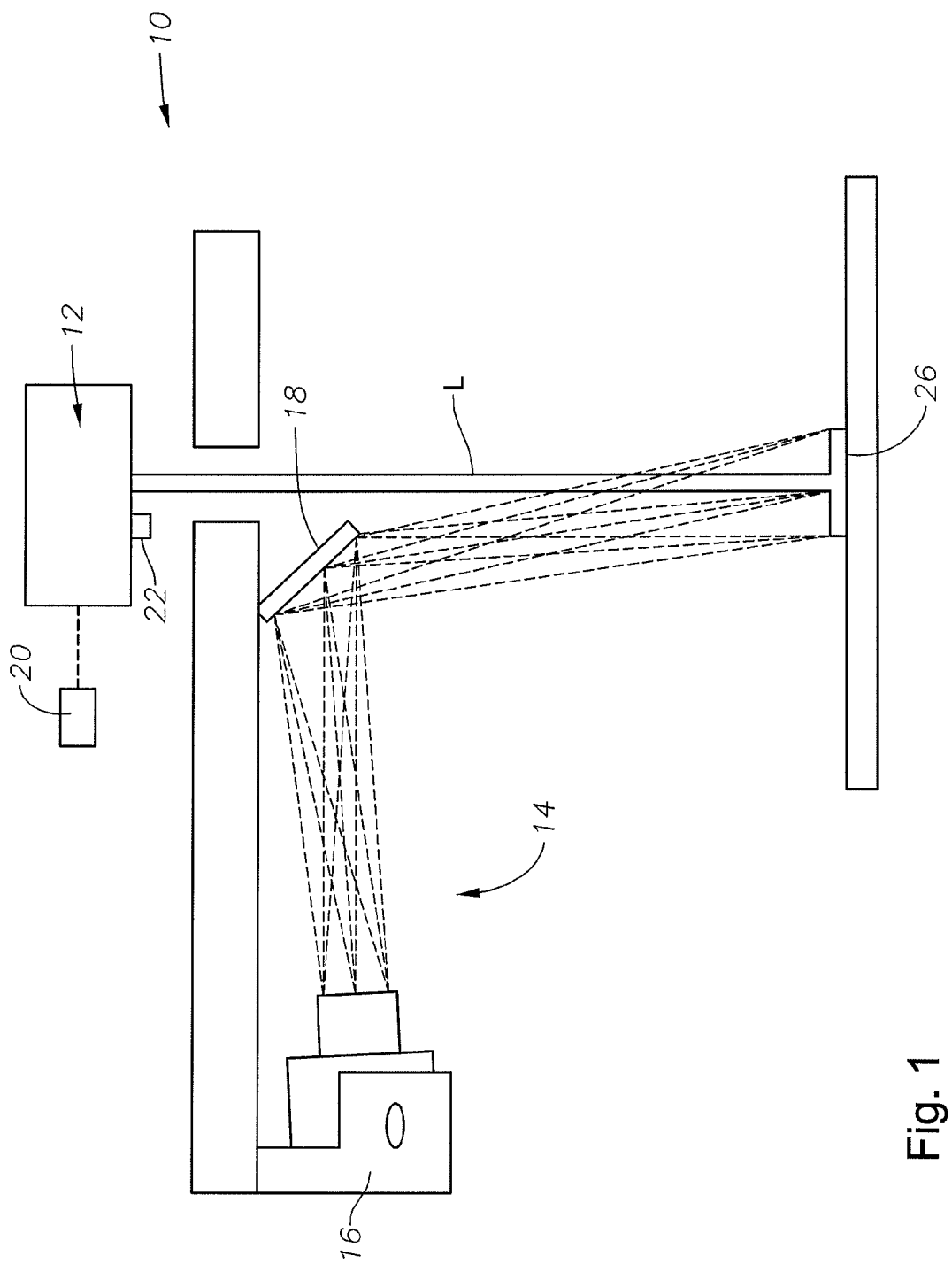
FIG. 1 shows a schematic representation of the system for surgical treatment of an eye.

A system 10 illustrated in FIG. 1 for surgical treatment of an eye includes a laser arrangement 12 with an argon-fluoride excimer laser which emits ultraviolet light with a wavelength of 193 nm. The laser arrangement 12 operates with a repetition-rate of 1050 Hz. However, a laser arrangement with a lower repetition-rate of, for example, 200 Hz to 750 Hz may come into operation in the system 10.

Furthermore, the system 10 is equipped with a temperature-registration device 14. The temperature-registration device 14 includes a thermal-imaging camera 16 which on the basis of IR radiation supplied to it is able to perform temperature measurements in non-contacting manner. Furthermore, the temperature-registration device 14 includes a deflecting device 18 for deflecting the IR radiation conducted to the thermal-imaging camera 16. In the exemplary embodiment that is shown in FIG. 1 of a system 10 for surgical treatment of an eye, the deflecting device 18 consists of a mirror coated with silver, aluminium or gold, which is arranged in the beam path of the IR radiation conducted to the thermal-imaging camera 16.

The laser arrangement 12 includes a control device 20 which serves to control the operation of the laser arrangement 12 and, in particular, the pulse energy of the laser arrangement 12. Furthermore, the control device 20 controls a scanner 22 provided with two deflection axes. The scanner 22 serves to move the light emitted from the laser arrangement 12, i.e. the laser beam L, over a surface of an object 26 to be subjected to the light of the laser arrangement 12, i.e. the laser beam L.

In the following, the calibration and also the operation of the system 10 illustrated in FIG. 1 for surgical treatment of an eye will be elucidated. As illustrated in FIG. 2, after the start-up of the system 10 a check is firstly made as to whether a calibration of the system 10 is required. For example, a calibration of the system 10 may be deemed to be necessary when the system 10 is first switched on or after a defined number of treatments carried out by means of the system 10 or after a predetermined number of hours of operation of the system 10. Furthermore, a fault message that is output by the system 10 may make a calibration of the system necessary. Finally, it is also conceivable that an operator of the system 10 may decide to carry out a calibration of the system 10.

If, in the test step described above, it is established that a calibration of the system 10 is required, a calibration process described in the following is carried out. Within the scope of this calibration process, firstly an initial temperature of a test object is registered by means of the thermal-imaging camera 16. By way of test object, a test object consisting of a plastic material, in particular of polymethyl methacrylate, may find application, for example.

Subsequently the test object is subjected to the laser beam L emitted from the laser arrangement 12. During the application of the laser beam L to the test object the temperature of the test object is registered continuously by means of the thermal-imaging camera 16.

In case of the registration of the initial temperature of the test object the temperature measurement is undertaken, just as in the case of the continuous registration of the temperature of the test object during the application of the laser beam L to the test object, over a defined area of the test object, which exhibits a size of, for example, 20 mm×20 mm. For each temperature measurement, three measurements at intervals of, for example, 5 seconds over a period of, for example, 0.5 seconds are carried out, and the measured values are averaged. The mean value derived from these three measurements is then regarded in each instance as the temperature value of the test object.

Furthermore, the achieved resection depth of the test object is registered as a function of the pulse energy of the laser arrangement 12, and these values are correlated with the measured temperature values of the test object. Finally, the calibration measurement for creating a set of parameters for a monitoring program for monitoring the laser arrangement 12 on the basis of the correlation of the pulse energy of the laser arrangement 12 with the resection depth of the test object is utilised, taking into consideration the temperature of the test object. In other words, a set of parameters is created that makes it possible to control the laser arrangement 12, i.e. in particular the pulse energy of the laser arrangement 12, in such a way that a desired resection depth is achieved but at the same time a desired maximal temperature of an eye to be treated is not exceeded. It will be understood that in the course of the creation of the parameters the data registered within the scope of the calibration measurement for the test object have to be corrected, taking into consideration the material properties of the test object and of the part of an eye to be treated, for example the cornea of an eye. The result of the calibration of the system 10 is consequently a set of parameters that makes it possible to control the pulse energy of the laser arrangement 12 that is required for achieving a desired resection depth, already taking into consideration the effects of the laser beam L on the temperature of an eye to be treated with the laser beam L.

In the course of the implementation of a process, illustrated in FIG. 2 on the right-hand side, for surgical treatment of an eye, firstly the initial temperature of the eye to be treated, i.e. in particular the initial temperature of the cornea of the eye, is registered. This temperature measurement is undertaken by means of the thermal-imaging camera 16. If desired or required, the initial temperature of the eye can be adjusted, for example reduced by cooling of the eye or of the cornea of the eye.

Subsequently the eye is subjected to the laser beam L, the temperature of the eye being registered continuously by means of the thermal-imaging camera 16 during the application to the eye of the laser beam L emitted from the laser arrangement 12. The pulse energy of the laser arrangement 12 is controlled in this case by the set of parameters created within the scope of the calibration process described above. Furthermore, the pulse energy of the laser arrangement 12 is reduced by the control arrangement 20 or an ablation region is headed for again at a later time if the temperature of the eye exceeds a predetermined limiting value. In this manner, thermal damage to the eye is reliably avoided.

The invention claimed is:

1. An apparatus for surgical treatment of an eye comprising:
   a laser arrangement adapted to emit light with a wavelength and repetition-rate suitable for surgical treatment of the eye and to emit the light towards a test object distinct from the eye;
   a temperature-registration device adapted to register the temperature of the test object; and
   a control device adapted to:
      register an achieved resection depth of the test object as a function of a pulse energy of the laser arrangement;
      correlate the resection depth and the pulse energy with the temperature to calibrate the apparatus;
      register a current temperature of the eye with the temperature-registration device;
      determine the pulse energy required to achieve a desired resection depth at the current temperature according to the correlated resection depth, pulse energy, and temperature; and
      control the laser arrangement to use the determined pulse energy to achieve the desired resection depth at the current temperature.

2. The apparatus according to claim 1, wherein the temperature-registration device is adapted to register the temperature of the test object before or during the application of the light of the laser arrangement to the object.

3. The apparatus according to claim 1, wherein the control device is adapted to receive a temperature signal that is output by the temperature-registration device and to control the laser arrangement as a function of the temperature signal.

4. A process for surgical treatment of an eye, comprising:
   subjecting a test object to light that is emitted from a laser arrangement with a wavelength and repetition-rate suitable for surgical treatment of the eye, the test object distinct from the eye;
   registering the temperature of the test object;
   registering an achieved resection depth of the object as a function of a pulse energy of the laser arrangement;
   correlating the resection depth and the pulse energy with the temperature to calibrate the laser arrangement;
   registering a current temperature of the eye;
   determining the pulse energy required to achieve a desired resection depth at the current temperature according to the correlated resection depth, pulse energy, and temperature; and
   controlling the laser arrangement to use the determined pulse energy to achieve the desired resection depth at the current temperature.

5. The process according to claim 4, wherein the registering the temperature of the object further comprises:
   registering the temperature of the test object before or during the application of the light of the laser arrangement to the eye.

6. The process according to claim 4, wherein controlling the pulse energy further comprises:
   controlling the pulse energy as a function of a temperature signal that is output by the temperature-registration device.

7. The process according to claim 4, wherein controlling the pulse energy further comprises:
   reducing the pulse energy of the laser arrangement if the predetermined limiting temperature of the eye is exceeded.

8. A process for calibrating an apparatus for surgical treatment of an eye, comprising:
   subjecting a test object to light that is emitted from a laser arrangement with a wavelength and repetition-rate suitable for surgical treatment of the eye, the test object distinct from the eye;
   registering the temperature of the test object;
   registering an achieved resection depth of the test object as a function of a pulse energy of the laser arrangement;
   correlating the resection depth and the pulse energy with the temperature to calibrate the apparatus;
   registering a current temperature of the eye;
   determining the pulse energy required to achieve a desired resection depth at the current temperature according to the correlated resection depth, pulse energy, and temperature; and
   controlling the laser arrangement to use the determined pulse energy to achieve the desired resection depth at the current temperature.

9. Process according to claim 8, wherein the registering the temperature of the test object further comprises:
   registering the temperature of the test object before or during the application of the light of the laser arrangement to the test object.

10. The process according to claim 8, further comprising:
adjusting a specified resection depth of the test object as a function of the temperature of the test object.

11. The process according to claim 8, further comprising:
creating a set of parameters for controlling the laser arrangement during the surgical treatment of the eye based on the correlation of the resection depth and the pulse energy with the temperature.

12. The process according to claim 11, further comprising:
determining the pulse energy of the laser arrangement that is required for achieving a desired treatment outcome according to the set of parameters.

13. The apparatus according to claim 1, further comprising:
a deflecting device adapted to deflect an infrared radiation emitted from the test object towards the temperature-registration device, wherein
the temperature-registration device comprises a thermal-imaging camera adapted to register the temperature of the test object using the infrared radiation.

14. The apparatus according to claim 1, the control device adapted to:
delay ablation to a later time to achieve the resection depth in the eye and such that the current temperature does not exceed a predetermined limiting temperature.

* * * * *